(12) United States Patent
Peschl et al.

(10) Patent No.: US 11,485,942 B2
(45) Date of Patent: Nov. 1, 2022

(54) LAMP MODULE COMPRISING LIGHT-EMITTING DIODES AND PHOTOREACTOR

(71) Applicant: Peschl Ultraviolet GmbH, Mainz (DE)

(72) Inventors: Alexander Peschl, Mainz (DE); Dirk Ziegenbalg, Ulm (DE)

(73) Assignee: Peschl Ultraviolet GmbH, Mainz (DE)

( * ) Notice: Subject to any disclaimer, the term of this patent is extended or adjusted under 35 U.S.C. 154(b) by 0 days.

(21) Appl. No.: 17/609,016

(22) PCT Filed: May 11, 2020

(86) PCT No.: PCT/EP2020/000094
§ 371 (c)(1),
(2) Date: Nov. 5, 2021

(87) PCT Pub. No.: WO2020/228980
PCT Pub. Date: Nov. 19, 2020

(65) Prior Publication Data
US 2022/0204898 A1 Jun. 30, 2022

(30) Foreign Application Priority Data
May 10, 2019 (DE) ..................... 10 2019 003 299.3

(51) Int. Cl.
*C12M 1/00* (2006.01)
*F21K 9/235* (2016.01)
(Continued)

(52) U.S. Cl.
CPC ............ *C12M 21/02* (2013.01); *C12M 31/10* (2013.01); *F21K 9/235* (2016.08); *F21K 9/237* (2016.08);
(Continued)

(58) Field of Classification Search
CPC ....... C12M 31/10; C12M 21/02; F21K 9/237; F21Y 2115/10
See application file for complete search history.

(56) References Cited

U.S. PATENT DOCUMENTS

2009/0016072 A1 1/2009 Lee et al.
2010/0267125 A1 10/2010 Erb et al.

FOREIGN PATENT DOCUMENTS

DE 20 2010 014 116 1/2011
DE 10 2010 042 670 4/2012
(Continued)

*Primary Examiner* — Karabi Guharay
(74) *Attorney, Agent, or Firm* — Gudrun E. Huckett

(57) ABSTRACT

The invention relates to a lamp module (10) which is designed to be used as an immersion radiator in photochemical reactors. The lamp module has a support body (3) with at least one light-emitting diode (LED) (1), a head part (12) for electrically connecting the at least one LED (1) and for mounting the support body (3), and an immersion tube (11) that delimits an area (19) in which the support body (3) is arranged together with the at least one LED (1). The area (19) delimited by the immersion tube (11) is filled with an electrically non-conductive liquid (100), which is transparent to the wavelengths of the radiation emitted by the LEDs (1) of the lamp module (10), such that the at least one LED (1) is completely immersed into the non-conductive liquid (100), wherein the head part (12) has connection lines (18, 18) which communicate with the area (19) for supplying and discharging the non-conductive liquid (100), and the support body (3) is designed as a heat sink which delimits at least one internal fluid path as a supply section (4) for the non-conductive liquid (100). The supply section (4) is connected to one of the connection lines (18, 18') via the head part (12) and opens into the area (19) on the support body (3) side facing away from the head part (12). The (Continued)

invention additionally relates to a photoreactor which is equipped with a corresponding lamp module.

17 Claims, 10 Drawing Sheets

(51) Int. Cl.
    *F21K 9/237*     (2016.01)
    *G01F 1/84*     (2006.01)
    *F21Y 115/10*     (2016.01)

(52) U.S. Cl.
    CPC ......... *G01F 1/8409* (2013.01); *F21Y 2115/10* (2016.08)

(56) References Cited

FOREIGN PATENT DOCUMENTS

| | | |
|---|---|---|
| DE | 10 2014 012 217 | 2/2016 |
| DE | 10 2014 012 218 | 2/2016 |
| DE | 10 2014 012 219 | 2/2016 |
| EP | 3885034 A1 * | 9/2021 |

* cited by examiner

LAMP MODULE COMPRISING LIGHT-EMITTING DIODES AND PHOTOREACTOR

BACKGROUND OF THE INVENTION

The invention concerns a lamp module comprising light-emitting diodes (LEDs), that can be used as an immersion radiator in photoreactors for performing photochemical reactions or also in so-called AOPs ("advanced oxidation processes") as well as for disinfection purposes, as well as a corresponding photoreactor.

It is known from the prior art to use radiation sources, in particular also UV radiators, as immersion lamps in a liquid medium in order to e.g. disinfect water or perform photochemical reactions. Conventionally, in general low pressure or medium pressure radiators (discharge lamps) are used that, e.g. for protection from soiling, are enveloped by an immersion pipe that is transparent for the radiation that is emitted or relevant for the photochemical reaction. The emission spectrum of the discharge lamps can be varied by suitable doping and adapted to a certain degree in accordance with the requirements for the photochemical reaction. However, the use of low pressure or medium pressure radiators entails high current consumption, and the radiation intensity decreases significantly with increasing age; moreover, the radiation spectrum can shift which requires a regular monitoring in relatively short time intervals.

In the illuminant field, LEDs increasingly gain importance due to their comparatively minimal current consumption, long service life, and the high switching capability at spontaneously full lighting current. The LED radiates light, infrared or UV radiation, when electrical current flows in forward direction. The wavelength of the emitted radiation depends on doping of the semiconductor component. For UV radiation, diamond, aluminum nitride, aluminum gallium nitride or aluminum gallium indium nitride are conceivable, for example.

Even though LEDs are no thermal radiators such as medium pressure radiators, high temperatures—usually caused by high currents required for a maximum light yield—shorten the service life of the LEDs significantly. In order to avoid this disadvantageous effect of higher temperature at higher currents, LEDs are frequently not operated at nominal power but below—in conjunction with reduced illumination power. In order to achieve a desired light quantity despite of this, the number of employed LEDs is then increased.

When the LEDs are to be operated for a high light yield or radiation intensity at high currents, an effective heat dissipation is required in order to maintain the service life of the LEDs. Frequently, metal housings, usually of aluminum, are employed for heat dissipation.

An illuminant with at least one luminescence diode that is surrounded in a self-contained housing with an electrically non-conductive transparent liquid for heat discharge is described in DE 20 2010 014 116 U1. The liquid serves for heat transportation from the diode to the housing from where the heat can radiate across a large surface area. By means of a pump, the liquid can be circulated in the housing in order to transport the heated liquid away from the diode to the housing wall where the heat can radiate into the environment.

For the use of LEDs in photobioreactors for culturing microorganisms, in US 2010/0267125 A1 an LED light module is described in which the LEDs are cooled by means of a support pipe that is surrounded by a transparent envelope pipe. In bioreactors, pressure and temperature conditions exist in the reaction chamber that do not differ significantly from ambient pressure and room temperature because only in this way an optimal growth of microorganisms can be usually achieved. When LEDs are to be used in photoreactors for chemical syntheses, e.g. photochlorination or photobromination, a corresponding lamp module of an immersion lamp must fulfill the increased requirements with regard to the surrounding reaction conditions which may deviate very distinctly from ambient pressure and room temperature.

DE 10 2010 042 670 A1 discloses a double-wall immersion pipe for thermal decoupling of a radiation source from the surrounding reaction chamber.

EP 3 183 493 B1 discloses an LED lamp module that is improved in respect to handling of the heat balance, that can be used not only under ambient conditions and in a laboratory scale but as immersion pipe for photochemical synthesis or photocatalytic synthesis, in AOPs as well as for disinfection, even in industrial scale. This lamp module comprises a cooling body having arranged at its outer side support structures with LEDs and comprising an inwardly positioned fluid path for a cooling agent circuit and delimiting a chamber for a current supply/control line. The cooling body with the LEDs is arranged in a double-wall immersion pipe of a material that is transparent for the wavelengths of the radiation that is emitted by the LEDs of the lamp module. For improving the thermal decoupling with the double-wall immersion pipe, the intermediately positioned gap can be evacuated or can be flushed with a cooling liquid. Moreover, the generation of an inert gas atmosphere in the immersion pipe with a certain excess pressure in relation to the ambient pressure is described therein for improving the explosion protection.

Based on this prior art, it is object of the present invention to provide a further improved lamp module with LEDs.

SUMMARY OF THE INVENTION

This object is solved by a lamp module that is configured to be used as an immersion radiator in photochemical reactors, that comprises a support body with at least one light-emitting diode (LED) and a head part for electrical connection of the at least one LED and for holding the support body; and that further comprises an immersion pipe that delimits an area in which the support body with the at least one LED is arranged, and that is characterized in that the area delimited by the immersion pipe is filled with an electrically non-conductive liquid, which is transparent for the wavelengths of the radiation emitted by the LEDs of the lamp module; in that the at least one LED is immersed completely in the non-conductive liquid; wherein the head part comprises connection lines, communicating with the area, for the supply and the discharge of the non-conductive liquid, and the support body is configured as a cooling body that delimits at least one internal fluid path as supply section for the non-conductive liquid, wherein the supply section is connected through the head part to one of the connection lines and opens at a side of the support body facing away from the head part into the area.

Further embodiments are disclosed in the dependent claims.

The further object of providing a photoreactor with LEDs as radiation source is solved by the photoreactor with a lamp arranged therein with an emission spectrum suitable for the photochemical reaction, characterized in that the lamp is a lamp module according to the invention.

An embodiment of a lamp module according to the invention that is configured to be used as an immersion radiator in photochemical reactors comprises a support body with one or a plurality of light-emitting diode (LED). The LED(s) can be fastened directly at the support body or on one or a plurality of support circuit board(s) that is or are arranged at the outer side of the support body. Moreover, the lamp module comprises a head part for electrical connection of the at least one LED and for holding the support body, as well as an immersion pipe that delimits an area in which the support body with the at least one LED is arranged for protection of the LEDs from the reaction conditions in the surrounding reaction chamber. According to the invention, this area delimited by the immersion pipe is filled such with an electrically non-conductive, i.e., electrically insulating, liquid that the one or plurality of LED(s) is/are immersed completely in the electrically non-conductive liquid. In this context, the electrically non-conductive liquid is selected such that it is transparent for at least one wavelength of the radiation emitted by the LEDs of the lamp module and provided for the task to be performed by the lamp module.

In order to achieve an optimal cooling of the LEDs in that not only the heat generated by the LEDs but also the heat caused by exothermic reactions is discharged with the non-conductive liquid from the reaction chamber that surrounds the immersion pipe, the head part comprises connection lines for the supply and the discharge of the non-conductive liquid which communicate with the area delimited by the immersion pipe. In this context, the support body is configured as a cooling body which delimits at least one internal fluid path as supply section for the non-conductive liquid, wherein the supply section is connected via the head part to one of the connection lines and opens at a side of the support body facing away from the head part into the area delimited by the immersion pipe. In this way, already upon passing the supply section through the support body, the non-conductive liquid supplied through a first connection line can absorb the heat which is generated by the LEDs, flows upwardly in the immersion pipe along the surface of the support body with the LEDs after exiting at the bottom end of the support body, wherein the non-conductive liquid not only can further absorb heat from the LEDs but also heat from the reactor environment before it is discharged through the second connection line from the immersion pipe area in order to dissipate the absorbed heat outside of the reactor environment.

Of course, more than one supply section through the support body may be provided; depending on the number and arrangement of the LEDs, a supply section through the support body can be provided for each axial LED row, for example.

Thus, this lamp module is improved with respect to cooling of the LEDs and the thermal decoupling from the environment, and it provides moreover an increased total light or radiation output in relation to lamps according to the prior art because, due to the non-conductive liquid, the photon outcoupling efficiency at the phase boundary diode surface—immersion pipe interior is increased and the reflection at the phase boundary immersion pipe interior—immersion pipe wall is reduced. This effect is detectable visually when using the lamp module in that the immersion pipe essentially becomes invisible to the eye.

Since the non-conductive liquid in the immersion pipe interior is permanently exchanged, the heat absorbed from the LEDs and the immersion pipe environment can be discharged and the temperature can be kept constant. Particularly preferred, a circulation of the non-conductive liquid can be provided in this context such that the non-conductive liquid heated in the immersion pipe is circulated in order to discharge the absorbed heat again outside of the immersion pipe interior.

For this purpose, it is provided in a further embodiment that the connection lines for supply and discharge are connected to each other for forming the circuit which comprises moreover at least one heat exchanger and a conveying device such as a pump and, as needed, a shut-off fitting/valve.

In the present application, the "electrically non-conductive liquid" is referred to for short as "non-conductive liquid" wherein the electrical non-conductivity is always intended however. Heat can be transferred from, to, and through this non-conductive liquid. All liquids that comprise a transmission level of at least 75% for the at least one wavelength of the radiation emitted by the LEDs of the lamp module along the shortest travel path between LED surface and immersion pipe inner wall are to be understood as "transparent".

Advantageously, by the immersion into the non-conductive liquid not only a cooling of the LEDs is provided, which contributes to prolonging their service life, but, due to the refractive index of the non-conductive liquid that is significantly greater than that of air or inert gas and lies in the range of approximately 1.35 to approximately 1.55 (at 20° C.) for suitable non-conductive liquids, the photon outcoupling efficiency at the phase boundary diode surface—immersion pipe interior increased and the reflection at the phase boundary immersion pipe interior—immersion pipe wall reduced so that the total light output of the lamp module, i.e., the radiation quantity and density at the outer surface of the immersion pipe, is significantly increased.

Upon filling the area delimited by the immersion pipe, an explosive atmosphere is also prevented by the non-conductive liquid. In contrast to the use of an inert gas such as nitrogen, it is advantageous in this context that an accelerated aging of the primary optics of the LEDs is avoided because in particular in chemical facilities VOCs ("volatile organic compounds") are present which penetrate into the primary optics which are usually configured as silicone lens, cause them to become cloudy and thus lower the light yield. Since the primary optics according to the invention are no longer exposed to any gas-containing atmosphere but are shielded by the non-conductive liquid, the aging process is significantly slowed.

The LED of the lamp module is selected in accordance with the wavelength(s) for the task to be performed from different LEDs which, depending on their doping, differ with respect to the emitted radiation wavelengths and cover the visible light as well as infrared and UV spectrum. Accordingly, the non-conductive liquid is selected, depending on the respectively employed emission wavelength, from different non-conductive liquids that differ with respect to the absorption spectra so that the non-conductive liquid is transparent for the desired emission wavelength.

The lamp module according to the invention relates to LEDs as light source. In this context, all semiconductor components emitting light, also organic luminous diodes (OLEDs), are encompassed.

The immersion pipe is expediently manufactured of a material that is transparent for the wavelengths of the radiation emitted by the LEDs. In addition, the immersion pipe is designed with respect to material selection and shape to reaction pressures in the range of high vacuum to 6 bar excess pressure which may exist in the reaction chamber surrounding the immersion pipe. As materials, natural or synthetic quartz glass or quartz glass mixtures or borosilicate etc. are conceivable.

The immersion pipe can be closed at one end so that the closed end can be positioned in the reaction chamber of the surrounding photoreactor as it is frequently the case for vertical arrangement of immersion lamps; the immersion pipe can however also be open at both ends and can also be used horizontally in reactors wherein the open ends of the immersion pipe project essentially from the reaction chamber.

In order to separate the lamp module and the non-conductive liquid provided in the immersion pipe safely from the immersion pipe environment, the head part in an embodiment according to the invention can be connected seal-tightly to the open end of an immersion pipe that is closed at one end and is predominantly used in vertical arrangement in a reactor. For this purpose, corresponding sealing means, for example, at least one seal, can be arranged on at least one contact surface between head part and immersion pipe. Of course, a lamp module with an immersion pipe closed at one end whose open end is seal-tightly closed with the head part can also be arranged in orientations in a reactor that deviate from the vertical. When an immersion pipe that is open at both ends is used, one end is closed by the sealing head part and the other end by a corresponding closure part.

In this context, the sealing connection of the head part and the immersion pipe can be supported additionally in a springy fashion in order to dampen vibrations for avoiding glass-metal contact. In addition or as an alternative to this, a form-fit connection of the head part and the immersion pipe can be advantageous in order to avoid tensile stresses in the immersion pipe material. For example, the head part can be fastened by auxiliary fastening means such as, for example, flanges, rings, and disks, and spring-loaded connecting means at the immersion pipe.

In a preferred embodiment, the immersion pipe with the head part at the open end can comprise a cone-shaped collar widening away from the open end, which is held by a holding ring with a corresponding cone-shaped opening at a base ring by means of spring-loaded bolts. The head part is received in the open end of the immersion pipe and can be seal-tightly fastened by pivot latches, which can be brought into engagement with an annular groove at an inner wall of the immersion pipe, or preferably by a pressure ring whose opening has a diameter that is smaller than the diameter of the head part and which is arranged on the holding ring and together with the holding ring is held at a base ring by means of spring-loaded bolts. The fastening of the head part in the immersion pipe is required so that the head part is not forced by the pressure that the non-conductive liquid is exerting on the head part out of the immersion pipe and the non-conductive liquid cannot escape. This fastening could be omitted when the open end of the immersion pipe is surrounded by a closed housing that can be filled with the non-conductive liquid; however, in this way also the head part would be immersed in the non-conductive liquid so that the exchange or servicing of the LED lamp would entail an increased expenditure.

The cone-shaped collar can be fastened as a separate component at the open end of the immersion pipe or the immersion pipe can preferably be manufactured as one piece together with the cone-shaped widened collar at the open end. The fastening by means of the spring-loaded bolts improves the mechanical stability of the lamp module for the sealed arrangement of the head part and avoids tensile stresses in the immersion pipe material. The spring-loaded screw connections permit compensation of different expansions occurring, for example, with heat exposure so that the screw connections cannot become detached. As a cover, a cover plate can be connected to the base ring wherein, as needed, a cylindrical housing can be inserted in order to be able to flush, for avoiding ignition sources, with an inert gas such as nitrogen the space above the open immersion pipe end with the head part, from where the connection lines for the non-conductive liquid and electrical connection devices extend. As an alternative, this space, as described above, could be filled with the non-conductive liquid.

In order to prevent that the heat that is absorbed by the non-conductive liquid from the LEDs is dissipated through the immersion pipe to the immersion pipe environment or the reaction medium which is present thereat, the head part or the support body or both can comprise heat dissipation structures such as ribs or fins etc. of a heat-conducting material which extend into the area delimited by the immersion pipe without covering the LEDs. This means orientation, arrangement, shape, and dimensions of such heat conducting structures are to be selected such that the radiation emitted by the LEDs is not prevented from exiting from the immersion pipe. The heat-conducting structures can extend through the head part out of the lamp module where the heat can be dissipated into the environment.

For guiding the non-conductive liquid, attention is to be paid that the flow rate, in particular for silicone oil, is to be kept minimal, i.e., preferably below 1 m/s, because otherwise a non-conductive product that is present in the photoreactor could lead to an electrostatic charge and thus the risk of an ignition source. In order to comply with the requirements for an ATEX certification with regard to ignition protection class "o"=oil encapsulation, the non-conductive liquid must have a kinematic viscosity (at 25° C.) of at least 20 cSt even through non-conductive liquids with minimal viscosity of, for example, 5 cSt, would be more advantageous technically in relation to the circulation and observance of surface temperatures of the LEDs.

Therefore, the non-conductive liquid can comprise a kinematic viscosity (at 25° C.) of 5 to 60 cSt wherein, in relation to the applicable standards with regard to explosion protection, a viscosity in the range of 20 to 50 cSt is preferred in order to obtain a corresponding certification. For use of non-conductive liquids with high viscosity, it is moreover advantageous to dimension the connection lines with sufficiently large diameter for avoiding internal pressure losses in order to avoid a pressure at the LEDs that is too high.

In order to maintain the surface limit temperature, the lamp module in a further embodiment can comprise for control of the flow rate in addition a flow meter which is connected to a control unit that is configured to control, depending on the flow rate value measured by the flow meter, a conveying device and/or fitting connected to one of the connection lines in order to maintain a predetermined flow rate of the non-conductive liquid through the immersion pipe interior along a surface of the LEDs. The control unit can be a separate unit, part of the flow meter, of the conveying device or of the fitting, or part of a superior control device of the lamp module. Preferably, due to the high viscosity required for explosion protection and the flow rate that is to be kept minimal, mass flow meters, for example, a Coriolis mass flow meter or floating body flow meter or other suitable measuring methods can be employed while vortex measuring devices are rather unsuitable.

The non-conductive liquid can be selected, for example, from highly refined mineral oils which comprise practically exclusively alkanes and cycloalkanes, i.e., saturated hydrocarbons. Advantageously, alkanes and cycloalkanes are transparent from the visible wavelength range to the far UV-C range (220-230 nm). Below, the transmission decreases but, in particular for sufficiently minimal thickness of the gap between the LEDs and the immersion pipe, can still be sufficient for wavelengths to 195 nm and below. Cycloalkanes may be preferred due to the higher refractive index in comparison to the corresponding linear alkanes. Thus, the refractive indices (20° C.) for $C_5$-$C_{14}$ cycloalkanes extend across a range of approximately 1.41 to 1.55 while the refractive indices (20° C.) for the corresponding linear $C_5$-$C_{14}$ alkanes cover a range of approximately 1.36 to approximately 1.43. Cyclohexane, for example, has a refractive index of approximately 1.43 while hexane has a refractive index of approximately 1.37. A disadvantage of the saturated hydrocarbons is primarily the formation of easily flammable vapor-air mixtures with a classification in the temperature class 3, which sets a maximum surface temperature of 200° C. for the operation in flammable atmospheres. Therefore, when using highly refined mineral oils as non-conductive liquid, care must be taken to provide a careful and seal-tight air exclusion in order to avoid the formation of such flammable vapor-air mixtures.

A preferred embodiment according to the invention can provide, as a non-conductive liquid, low viscosity silicone oils which comprise refractive indices in the range of approximately 1.37 to 1.40, are advantageously non-combustible, and are transparent from the visible wavelength range to the medium UV-C range (approximately 250 nm). Below 250 nm, the transmission begins to decrease however and wavelengths smaller than 200 nm are absorbed so that silicone oils are suitable primarily for applications that want to employ wavelengths greater than 250 nm. For applications that want to employ wavelengths in the range of 200 to 250 nm, silicone oils are suitable only to a limited extent, namely when the thickness of the liquid-filled gap between LED and immersion pipe and thus the absorption is small enough in order to provide for a sufficient transmission. Otherwise, saturated hydrocarbons should be used as non-conductive liquid.

Further alternative non-conductive liquids comprise synthetic ester and ether compounds. Synthetic organic ester oils, in comparison to the mineral oils, have inter alia the advantage of a higher temperature resistance and higher combustion and ignition temperature and are more environmentally compatible, but exhibit disadvantageously a reduced aging resistance and are transparent at most to the medium UV range (approximately 270 to 280 nm); below, the absorption decreases significantly. For ether compounds such as, for example, 1,4-dioxane with a refractive index of 1.422, the transmission only extends to the medium UV range (270 to 300 nm, aside from diethyl ether to 255 nm); below, the transmission however decreases less steeply so that ether compounds as non-conductive liquids can also be used for wavelengths below 270 for a sufficiently minimal layer thickness between LED and immersion pipe wall. Wavelength smaller than 220 nm are however absorbed. With regard to safety technology, it must however be taken into account that ether compounds form easily flammable vapor-air mixtures wherein great differences exist between the different ether compounds. Diethyl ether, for example, is classified in temperature class T4 (maximally permissible surface temperature 135° C.) while 1,4-dioxane is classified in temperature class 2 (maximally permissible surface temperature 300° C.) so that 1,4-dioxane can be used more likely as a non-conductive liquid.

Of course, also further liquids can be used in a lamp module according to the invention as long as they are electrically insulating and transparent for the wavelength emitted by the respective LEDs.

In order to provide the required transmission of at least 75% for the desired transparency even for wavelengths below 250 nm, a lamp module design can thus be advantageous in which the inner diameter of the immersion pipe in relation to the outer diameter of the support body furnished with the LEDs is selected such that the gap—and thus the absorption—between the LED surface and the immersion pipe inner wall is as small as possible.

In order to decouple the thermally sensitive LEDs from the conditions that are present in the surrounding reaction chamber and to not impair the functionality of the LEDs, the immersion pipe can be a double-wall immersion pipe, or the lamp module can comprise a second immersion pipe in which the first immersion pipe is arranged. The gap that is formed between the two immersion pipes or the double walls provides a thermal decoupling. The latter can still be reinforced in that with a suction device a vacuum is generated in the gap or in that a further cooling circuit is connected for fluid cooling in the gap. In the embodiment as a double-wall immersion pipe, the gap between the walls can even be evacuated already during its manufacture. As a cooling fluid, all media that do not absorb the emitted radiation of the LEDs are suitable, for example, water or gas, in particular inert gas but also air. Advantageously, due to the additional immersion pipe, the surface of the immersion lamp is enlarged and thus an increased photochemical efficiency is realized.

It is proposed to manufacture the immersion pipe(s) expediently of a material that is transparent for the wavelengths of the radiation emitted by the LEDs. In addition, with respect to material selection and shaping, the immersion pipe is designed for reaction pressures in the range of high vacuum to 6 bar excess pressure which may exist in the reaction chamber surrounding the immersion pipe. As materials, natural or synthetic quartz glass or quartz glass mixtures or borosilicate etc. are conceivable. Constructively, an immersion pipe can be designed in standard dimensions with a wall thickness in the range of approximately 3.5 mm, as needed, also above up to 4.5 mm. Depending on different parameters such as, for example, the employed immersion pipe material, dimensioning of the entire lamp module, or an intended pressure at use, the wall thickness of the immersion pipe can also deviate therefrom, i.e., the wall thickness of the immersion pipe is designed in accordance with the predetermined requirements. Thus, higher pressures can also require immersion pipe wall thicknesses that are greater than 4.5 mm or a miniaturized lamp module can comprise an immersion pipe wall thickness that is smaller than 3.5 mm. Furthermore, employed immersion pipes can be tempered once or multiple times and pressure-tested, for example, up to 10 bar.

In a further embodiment, the support body can comprise at least one inwardly positioned chamber that is delimited by the support body so that, through the chamber, at least one current supply and/or control line can extend from the head end of the support body to a contact element of the at least one LED. The contact element can be arranged, for example, in a recess in the wall of the support body that delimits the chamber so that contacting with the current supply and/or control line can be realized from the interior. However, in case the contact element is arranged at the outer side of the support body, the chamber, for contacting the current supply and/or control line, can have at least one opening to the outer side of the support body through which the at least one current supply and/or control line can pass. Entry of the non-conductive liquid through this opening into the chamber is permitted in this context so that in this way an additional cooling effect occurs. Alternatively, this opening can be sealed about the current supply and/or control line that is passing through in order to avoid entry of the non-conductive liquid into the chamber. Preferably, all electrical connections that are surrounded by the non-conductive liquid or come into contact therewith can be designed to be fluid-tight in order to avoid that the non-conductive liquid, as a result of creepage and capillary effects due to the surface tension, for example, between contact locations, where possibly the electrical contact is deteriorated or interrupted. In case of plug-in connections, sealed plugs may possibly suffice; as needed, further measures, for example, soldering of the contact locations, are required also in order to avoid not only in order creepage of the non-conductive liquid but also to ensure the electrical contact.

At the head part of the lamp module, electrical and mechanical connection devices can be provided. Electrical connection devices ensure the connection of the current supply and/or control line to a current supply and control device of the lamp module. The current supply and control device of the lamp module for the LEDs, which comprise, for example, ballast or power electronics, drivers, and power supply parts, can be an external current supply and control device that is connected by a first electrical connection device of the head part. Alternatively, the current supply and control device of the lamp module can be housed, as needed, in the head part—then the electrical connection device serves for connection to a current source. By means of a further electrical connection device, the current supply and/or control line is then connected to the head part.

Electrical connections through the head part are configured preferably water-tightly (or fluid-tightly) lengthwise in order to avoid that the non-conductive liquid passes through the lines out of the head part into the space above the open immersion pipe end and, for example, during manufacture of the head part, can be potted therewith so that no liquid can pass through the insulation or the shield of the electrical line to the exterior due to capillary effects. Preferably, the connection locations can be soldered here also.

For cooling a current supply and control device housed in the head part, the connection lines extending through the head part can be used and then comprise one or a plurality of cooling agent path(s).

For the mechanical holding of the lamp module, a mechanical connection device for connection of the head part to a corresponding holder is provided. All connection devices can be preferably configured as detachable plug-in, screw, plug-and-screw, clamping connections or the like so that the lamp module in a simple way can be separated from and joined again with the current supply and/or control line or device, the cooling agent lines, and the mechanical holder. Depending on the arrangement of the lamp module in the reactor (horizontal or vertical), holder and cooling agent line can be designed as rigid (pipe) connections (for example, in case of horizontal arrangement), or non-rigid hoses for the cooling agent lines and metal or plastic cables or chains for the holder are used (for example, in case of vertical arrangement) so that the LED lamp is essentially freely suspended from the head part, which facilitates handling of the lamp module.

Moreover, the lamp module can comprise a multitude of LEDs wherein a portion of the multitude of LEDs, respectively, are arranged respectively on a support circuit board and the support circuit boards are fastened to the support body. This makes it possible that, in case of failure of one LED on one circuit board, it is not necessary that all LEDs must be switched off but only the circuit board in question while the other circuit boards can continue to operate so that the exchange of the circuit board in question can wait until a reaction in the surrounding reactor has been carried out.

For this purpose, the lamp module can have a detection unit for each circuit board that is configured to determine a failure of one or a plurality of LEDs on the support circuit board and, depending on a determined failure, to interrupt the current supply for the circuit board in question and to limit it correspondingly for the further support circuit boards, as needed. As needed, by means of the control unit of the lamp module, a warning message can be issued also when the detection unit is connected to the current supply and control device of the lamp module. In principle, such a detection unit is also conceivable for each LED so that, in case of failure of individual LEDs, the respective current supply is interrupted and the current supply for the further LEDs can be correspondingly limited, as needed.

Moreover, the lamp module can comprise one or a plurality of temperature sensor(s) that is/are arranged on the support body and connected to the current supply and control device of the lamp module that comprises a protective switch for LEDs. The current supply and control device can furthermore comprise, alternatively or additionally, at least one control circuit for the LED control with which same or different LEDs can be dimmed and/or the spectrum of the emitted wavelengths of different LEDs can be changed in order to adjust the emitted light quantity or the emitted wavelengths to the course of the reaction in the surrounding reaction chamber.

A further embodiment of the lamp module according to the invention can provide that in one of the connection lines connected in a circuit, preferably at a highest location, a breathing unit with drying agent is provided in order to enable venting of the non-conductive liquid for avoiding condensed water, wherein introduction of moisture via fresh air can be avoided through a drying agent such as silica gel.

According to a further embodiment of the lamp module, at least one, preferably all LEDs of the lamp module can be designed without primary optic. Due to the non-conductive liquid that is present, the LED is already sufficiently protected against environmental effects so that the primary optics, which are subject to a certain aging process depending on the operating conditions, can be entirely omitted.

A photoreactor according to the invention comprises a reaction vessel that delimits a reaction chamber for performing a photochemical reaction of at least one educt that is supplied to the reaction vessel or placed therein. Moreover, it comprises at least one lamp module according to the invention arranged in the reaction vessel with an emission spectrum that is suitable for the photochemical reaction.

BRIEF DESCRIPTION OF THE DRAWINGS

Further embodiments as well as some of the advantages which are connected with these and further embodiments will become clear and better understood by the following detailed description with reference to the accompanying drawings. Articles or parts thereof which are substantially identical or similar may be provided with the same reference characters. The Figures are only a schematic representation of an embodiment of the invention.

It is shown herein in.

DESCRIPTION OF PREFERRED EMBODIMENTS

The device according to the invention is an LED lamp module that is configured to be used as an immersion radiator in a photoreactor and a corresponding photoreactor that is furnished with one or a plurality of LED lamp modules according to the invention.

The LED lamp module according to the invention is provided primarily for industrial use in the preparative photochemistry and must therefore fulfill the higher requirements. These include in particular reaction temperatures and pressures deviating from room temperature and ambient pressure, which exist in the reaction chamber around the lamp module and encompass also temperatures below +5° C. and above +40° C. as well as pressures in the range of high vacuum and 6 bar excess pressure. Moreover, in regard to the light sources which are used in the photoreactors, explosion protection—depending on the composition of the reaction volume—must be taken into account; in certain embodiments, the LED lamp modules according to the invention can also be used in ATEX-classified fields.

For the ATEX certification, a specification for insulating liquids is prescribed in DIN EN 60079-6, for which purpose a non-conductive liquid with a viscosity greater or equal to 20 cSt, for example, 50 cSt, must be selected. Viscosities that are lower are also realizable for a lamp module according to the invention, provided the requirements of the standard must not be fulfilled.

Figure 1:
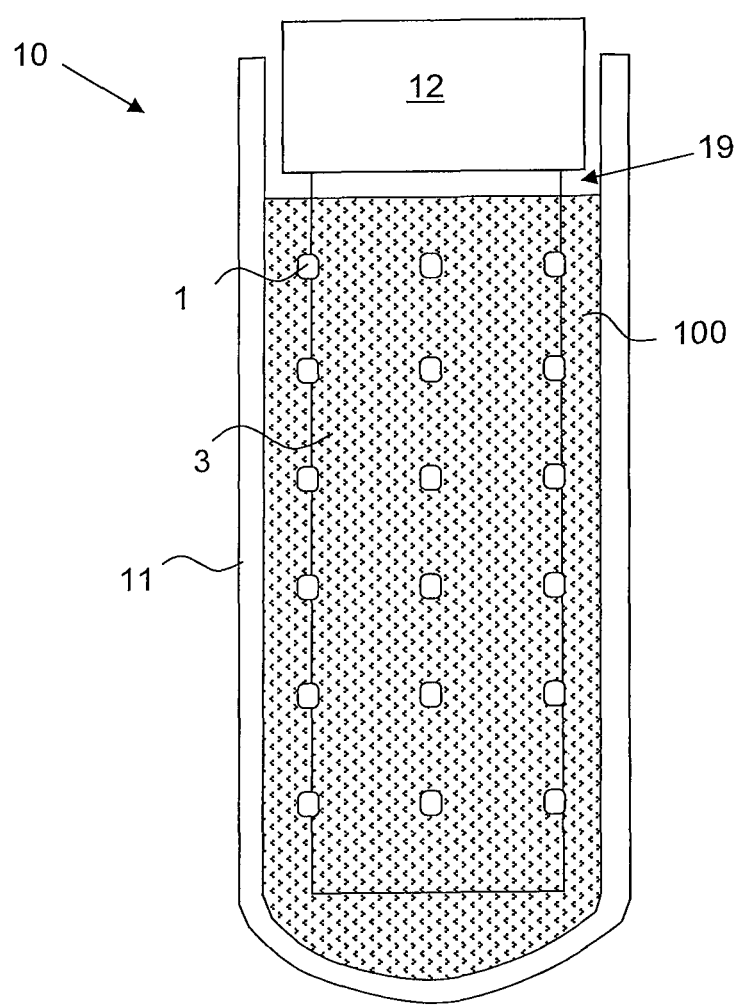
FIG. 1 a schematic side view of a first embodiment of an LED lamp module according to the invention.

FIG. 1 shows as an example a lamp module 10 that is designed as an immersion lamp for vertical arrangement in photochemical reactors. The lamp module 10 comprises a support body 3 having light-emitting diodes (LEDs) 1 arranged in distributed arrangement at its wall surface. The support body 3 is connected to a head part 12 that provides an electrical connection of the LEDs 1 and serves for holding the support body 3. Moreover, the lamp module 10 comprises an immersion pipe 11 of a material that is transparent for the wavelengths of the radiation emitted by the LEDs 1 and delimits an area 19 in which the support body 3 with the LEDs 1 is arranged. This area 19 is filled with a non-conductive liquid 100 so that the LEDs 1 are completely immersed. The non-conductive liquid 100 that is selected from saturated hydrocarbons, silicon oils, and synthetic ester and ether compounds is transparent in this context for the wavelengths of the radiation emitted by the LEDs 1 and comprises a refractive index (20° C.) in the range of at least 1.35 to approximately 1.45, as needed, also up to approximately 1.55. In this way, the photon outcoupling efficiency of each LED 1 is increased because fewer photons are reflected at the boundary layer between diode substrate and non-conductive liquid, and the reflection at the phase boundary between the non-conductive liquid 100 and immersion pipe wall 11 is reduced so that the total light output of the lamp module 10, i.e., the radiation quantity and density at the outer surface of the immersion pipe 11, is significantly increased. Moreover, the non-conductive liquid contributes to cooling of the LEDs 1 and thus to prolonging their service life.

Figure 2:
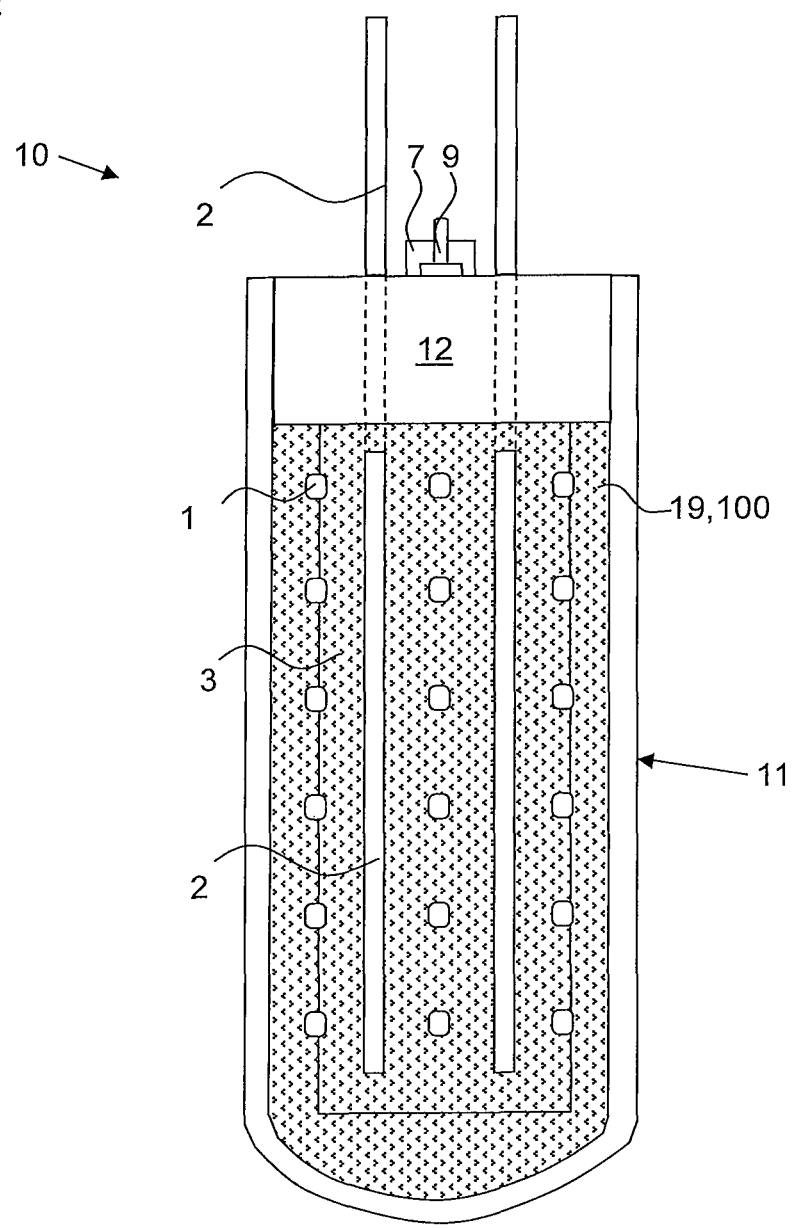
FIG. 2 a schematic side view of a further embodiment of an LED lamp module according to the invention.

The cooling efficiency through the non-conductive liquid can be improved by heat conducting structures at the head part and/or support body. FIG. 2 shows rib-like heat conducting structures 2 which are arranged along the support body 3 between vertical rows of LEDs 1 and can absorb the heat from the non-conductive liquid 100. The heat conducting structures 2 are extended in this context through the head part 12 to the exterior in order to discharge the dissipated heat to the environment. The head part 12 comprises moreover an electrical connection device 7 and a mechanical connection device 9 and is arranged at the open end of the immersion pipe 11. A corresponding holder 14 for connection to the mechanical connection device 9 is illustrated in FIG. 3.

The connection lines for circulation of the non-conductive liquid for discharging the heat absorbed from the LEDs 1 and from the reaction medium in the immersion pipe environment to the region outside of the immersion pipe 11 are not illustrated in FIGS. 1 and 2.

Figure 3:
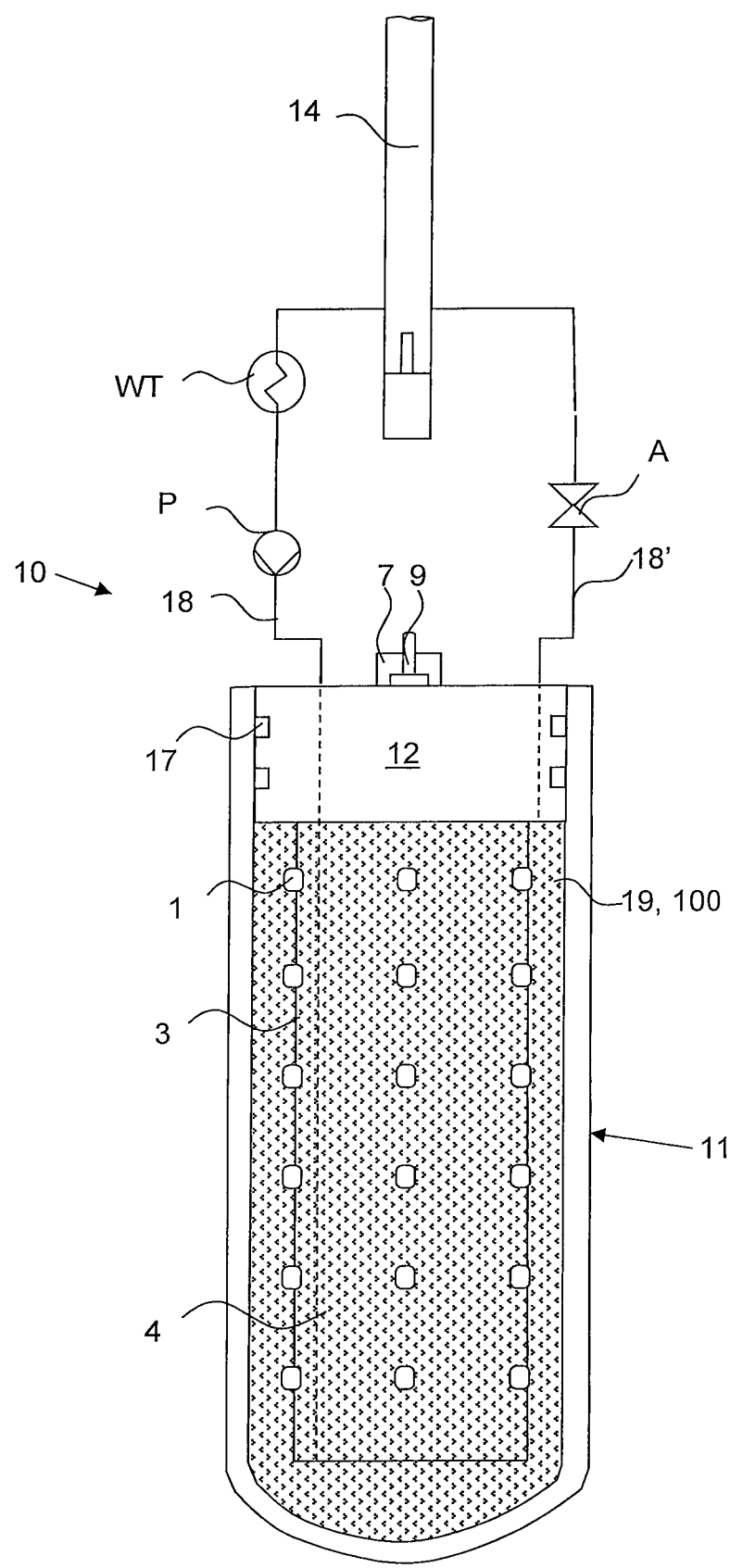
FIG. 3 a schematic side view of a further embodiment of an LED lamp module according to the invention.

For sealing the immersion pipe interior 19, the head part 12 can be connected seal-tightly to the open end of the immersion pipe 11, as this is indicated in FIG. 3 by the seals 17. Of course, deviations from the illustrated example in shape, arrangement, and sealing concept of the head part at the immersion pipe are possible and encompassed by the claimed subject matter. Thus, the head part can also project past the immersion pipe, for example, and the sealing action can be realized via the end face or the outer circumference of the immersion pipe.

An embodiment with a spring-supported connection of the head part to the immersion pipe for improving the mechanical stability of the lamp module as an immersion lamp is configured further below in connection with FIGS. 11 to 14. For this purpose, the head part comprises a collar on which an annular disk is arranged which is connected by spring screws to an annular flange arranged at the open end of the immersion pipe. For this purpose, the end section of the immersion pipe can be widened in upward direction in a cone shape and the annular flange can comprise a corresponding cone-shaped opening.

Moreover, FIG. 3 shows a circulation of the non-conductive liquid 100 that is supplied at the bottom end into the area 19 through the action of the pump P via a connection line 18, which extends through the head part 12 and is connected to the supply section 4 extending through the support body 3, and is discharged at the upper end of the area 19 via the connection line 18', which extends through the head part 12. A heat exchanger WT enables the dissipation of the heat absorbed by the non-conductive liquid 100. By means of the optional fitting A, pressure in the area 19 can be adjusted, as needed.

Figure 9:
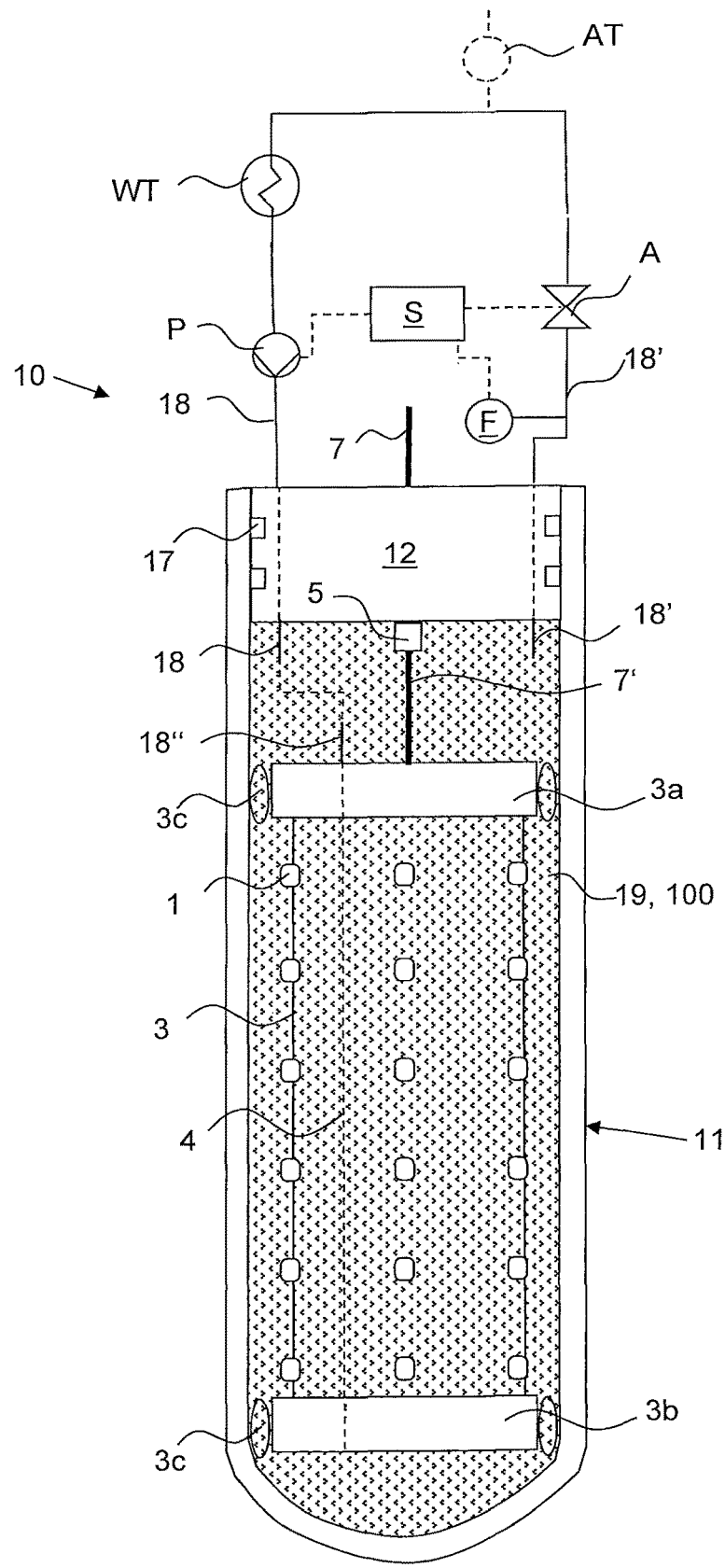
FIG. 9 a schematic side view of a further embodiment of an LED lamp module according to the invention.

For maintaining the surface limit temperature of the lamp module 10 during operation, it is expedient to monitor the flow volume of the circulated non-conductive liquid 100 that should not drop below a predetermined minimum value, for which purpose one or a plurality of flow meters can be arranged in the circuit. FIG. 9 shows in an exemplary fashion a flow meter F at the connection line 18' which is connected to a control unit S that controls pump P or preferably fitting A, as needed also both, for control of the flow rate of the non-conductive liquid 100. For the high viscosities and minimal flow rates required for the ATEX certification, Coriolis mass flow meters are suitable as flow meters that fulfill the safety level ("safety integrity level", for short SIL) for an ATEX certification. Alternatively, floating body flow meters can be used which also deliver reliable measured values at high viscosity and minimal flow rate of the non-conductive liquid 100 while vortex flow meters are less suitable.

Figure 4:
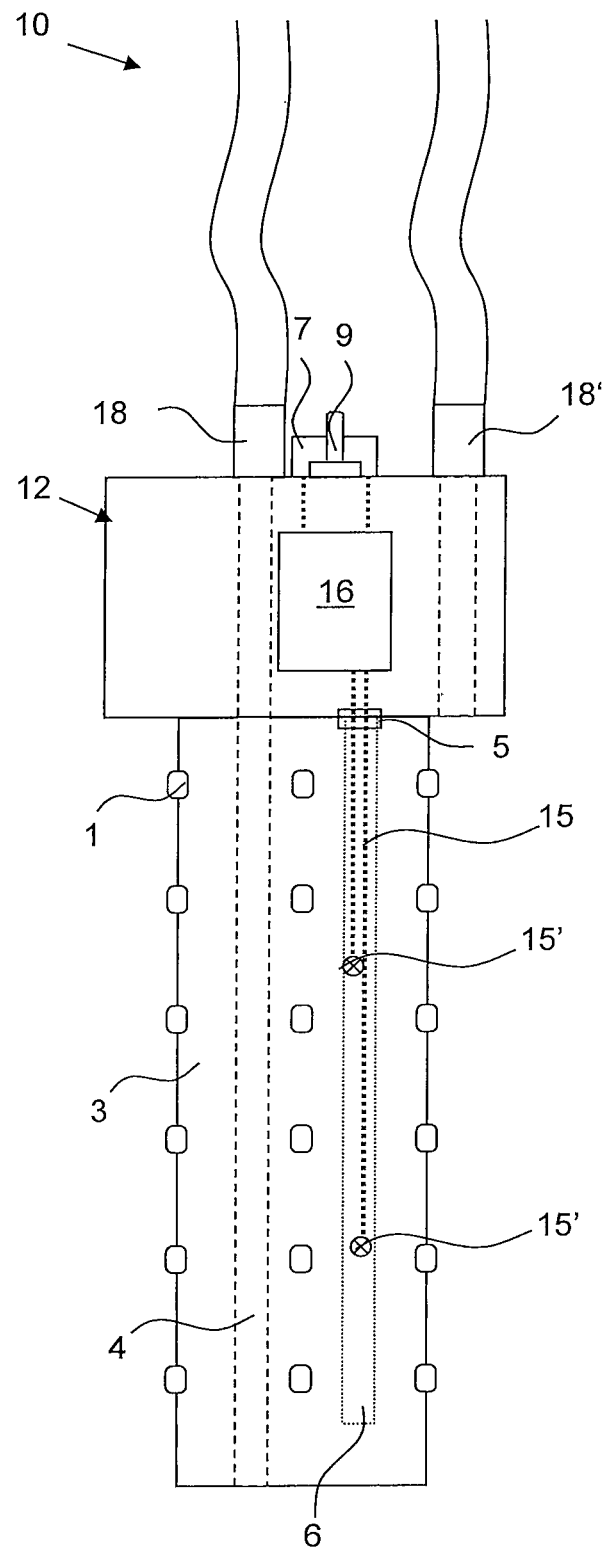
FIG. 4 a schematic side view of a support body with head part of a further embodiment of an LED lamp module according to the invention.

FIG. 4 shows embodiment variants of the support body 3 and of the head part 12. The support body 12 configured as a cooling body delimits with supply section 4 the internal fluid path for the non-conductive liquid 100. In this way, the LED(s) 1 or their support or cooling structures 1g (compare FIG. 8) are cooled essentially from the backside. The supply section 4 opens at the end of the support body 3 which is facing away from the head part into the bottom area of the immersion pipe 11 and flows from there externally along the surface of the support body 3 with the LEDs in upward direction in order to be discharged through the connection line 18'. Deviating from what is illustrated in FIG. 4, also more than one fluid path can be extended through the cooling body 3 in order to achieve an optimal cooling of the LEDs 1. Since the active cooling with the non-conductive liquid enables the use of modules with a plurality of LEDs or the operation of the LEDs at high power, a high power density is achieved which can compete with low and medium pressure radiators in the field of photochemistry. Manipulation and control of the heat balance—for short thermal management—of an LED lamp module that also must take into consideration the process temperature of the reaction medium that surrounds the lamp module is of decisive importance for an adequate service life.

The sections of the connection lines 18, 18' in the head part 12 serve in this context at the same time for cooling the current supply and control device 16, which is arranged in this example in the head part 12 and is connected, on the one hand, to the electrical connection device 7 and, on the other hand, to the current supply and/or control lines 15 extending through the chamber 6 that is located in the support body 3 for connection to the contact elements 15' of the LEDs 1 at different levels.

Figure 5:
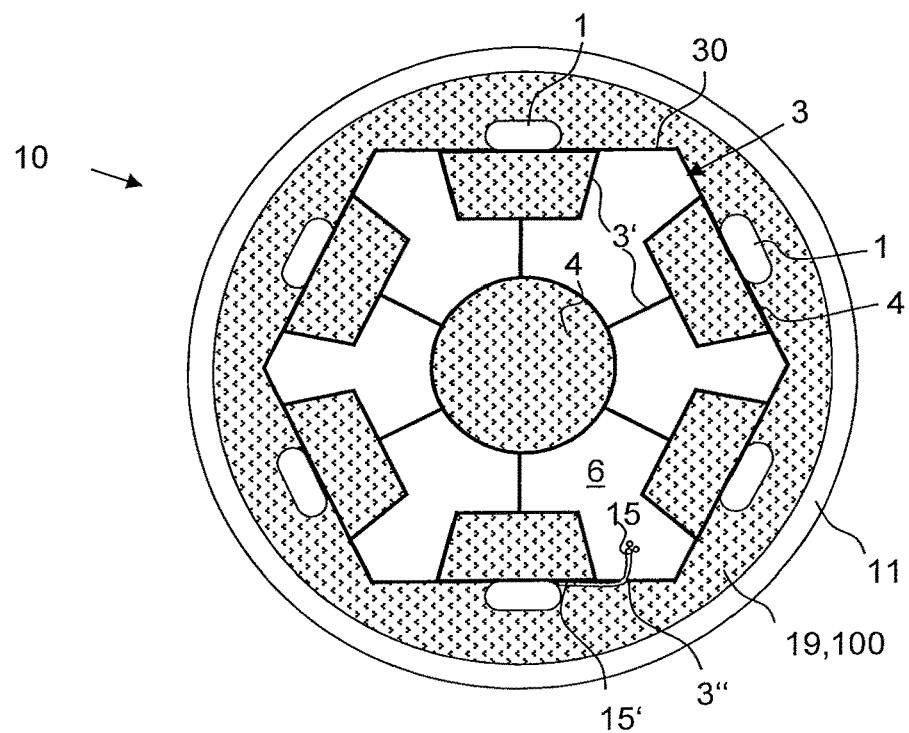
FIG. 5 a schematic cross section view of a further embodiment of an LED lamp module according to the invention.
Figure 6:
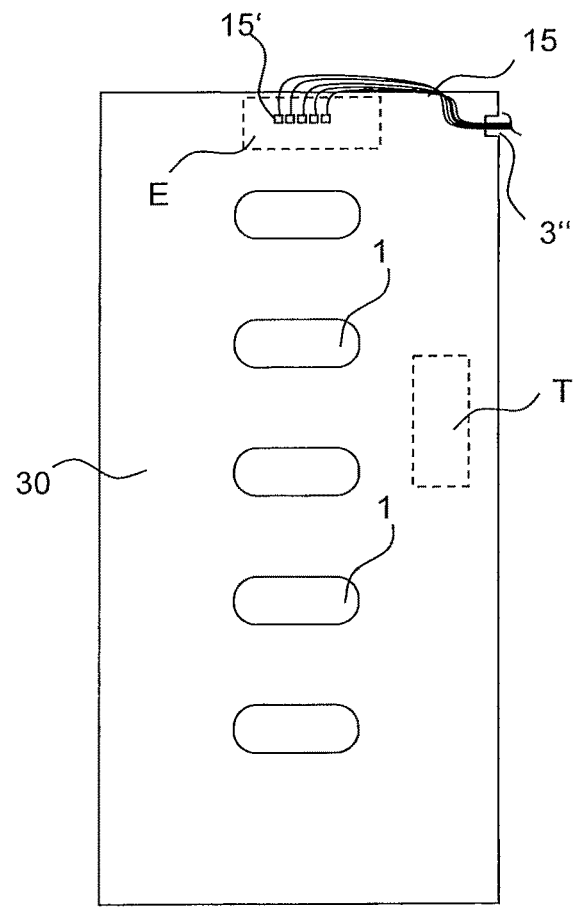
FIG. 6 a schematic plan view of a support circuit board with LEDs and contact element.

The chamber 6 and contact elements 15' can be seen also in the examples of FIGS. 5 and 6, wherein FIG. 5 shows an LED lamp module 10 whose support body 3 is configured as a hexagonal hollow profile, for example, of aluminum by extrusion molding, as cooling body with inwardly positioned supply channels 4. The supply channels 4 are connected in this context by webs 3' so that the intermediate spaces are available as cable chambers 6. Through an opening 3" in the outer wall of the support body 3, the current supply and/or control lines 15 are extended from the chamber 6 to the exterior to the contact elements 15' which here are arranged together at its end adjacent to the opening 3" for supply of the LEDs 1 arranged on a circuit board 30. All electrical contacts can be soldered in order to avoid penetration of the non-conductive liquid. The opening 3" can also be closed about the current supply and/or control line 15, for example, soldered, in order to avoid penetration of the non-conductive liquid into chamber 6. Alternatively or additionally, the connection 5 of the current supply and/or control line 15 to the head part 12 (compare FIG. 4) can be designed fluid-tightly lengthwise so that flooding of the chamber 6 with the non-conductive liquid may be permitted.

Since the radiation angle of conventional LEDs is limited, polygonal, for example, hexagonal or octagonal, profile cross sections of the support body are advantageous. When OLEDs are used, also circular cylindrical shapes can be realized well.

Figure 7:
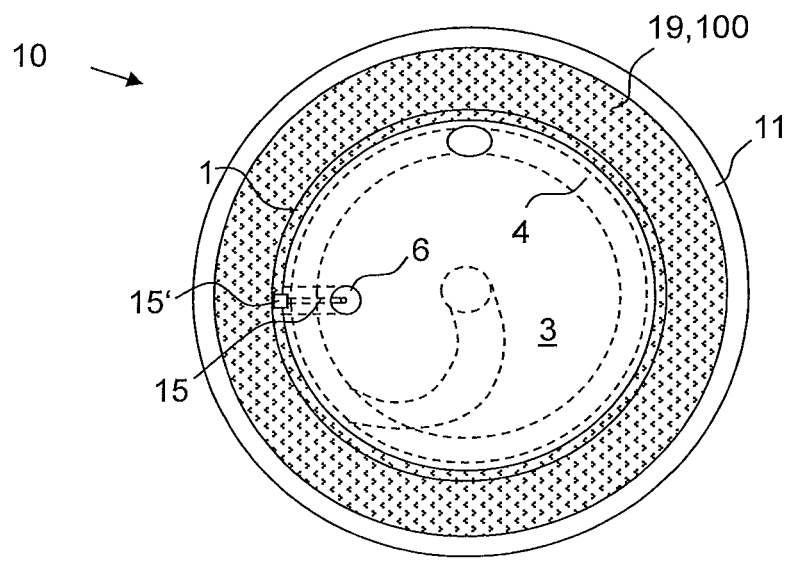
FIG. 7 a schematic cross section view of a further embodiment of an LED lamp module according to the invention.

FIG. 7 shows an OLED 1 that is arranged here as a layered composite on the cylindrical support body 3 and is immersed in the non-conductive liquid 100 in the immersion pipe 11. This support body 3 also comprises a cooling fluid path which is here configured however as a helical supply section 4 that comprises at the head part a lateral opening for connection to a connection line, not illustrated, and opens centrally at the bottom of the support body 3 in the opening that is without reference number and illustrated in dashed lines. For connection of the OLED at its contact element 15', a current supply and/or control line 15 extends here also through a chamber 6 within the support body 3.

In principle, all connecting locations, e.g. at the contact elements 15', the access 3" to the cable chambers 6, and at an electrical connection 5 at the head part 12 (see e.g. FIGS. 4, 9) can be configured water-tightly lengthwise in order to prevent that portions of the non-conductive liquid 100 can escape into the cable chambers 3 and further by capillary effects along electrical lines through the head part 12 to the exterior of the lamp module 10. For this purpose, measures, for example, potting of line sections in the head part and/or plug-in connections that are sealed by means of seals may be sufficient, as needed. However, in order to reliably prevent penetration of the non-conductive liquid, which in case of electrical plug-in connections can possibly also lead to interruption of the contact, the contact locations can be sealed by soldering, for example.

Figure 8A:
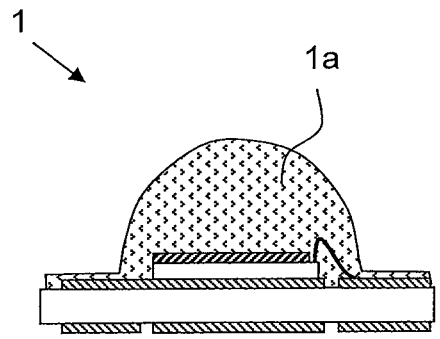
FIG. 8 a schematic cross section view of a conventional LED (a) and an LED without primary optic (b) of a lamp module according to an embodiment according to the invention.
Figure 8B:
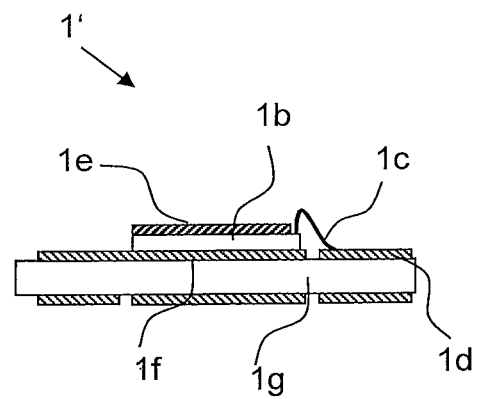

In FIG. 8, *a*) a conventional LED 1 with a plastic lens as a primary optic 1*a* is illustrated which can be used in an LED lamp module 10 according to the invention. FIG. 8*b*) shows an LED 1' without primary optic whose construction otherwise corresponds to the conventional LED 1 of FIG. 8*a*) with semiconductor crystal 1*b*, wire 1*c*, anode 1*d*, LED chip 1*e*, cathode 1*f*, and support 1*g* and which can be used in an LED lamp module 10 according to the invention because here the non-conductive liquid 100 takes on the function of the primary optic. Advantageously, the cooling effect can be further improved in this way, aside from saving a component.

FIG. 9 shows schematically an embodiment of the lamp module 10 according to the invention in which the support body 3 with the LEDs 1 is not directly connected to the head part 12. The support body 3 with the LEDs 1 comprises here at both sides a socket section 3a, 3b which facilitates by means of annular spring 3c the centered arrangement in the immersion pipe 11. The annular spring 3c permits the passage of the non-conductive liquid 100 past the socket 3a, 3b. In principle, the socket section 3a proximal to the head part is provided with a connection line section 18" which extends from the side of the socket section 3a facing the head part 12 through the socket section 3a to the supply section 4 in the support body 3. The supply section 4—of course, the connection line section 18" can also be connected with a distributor to several supply sections—opens at the side of the socket section 3b remote from the head part and facing away from the head part 12. The connection line section 18" is connected to the supplying connection line 18 while the discharging connection line 18' opens at the head part 12 into the interior 19.

Moreover, the upper socket section 3a comprises an electrical/electronic connection device 7' for current supply and control of the LEDs 1 which is connected by a connector 5 that is water-tightly sealed lengthwise to the connection device 7 of the head part 12 that is arranged, sealed by means of seals 17, in the open end of the immersion pipe 11.

Figure 10:
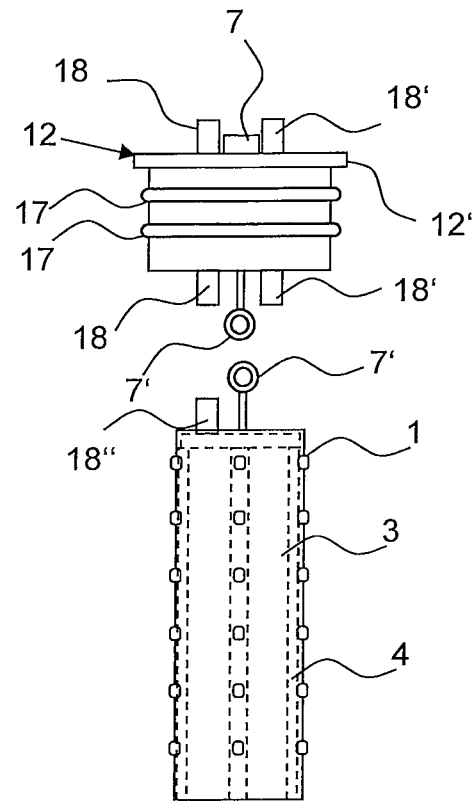
FIG. 10 a schematic side view of a head part and support body according to a further embodiment of an LED lamp module according to the invention.
Figure 15:
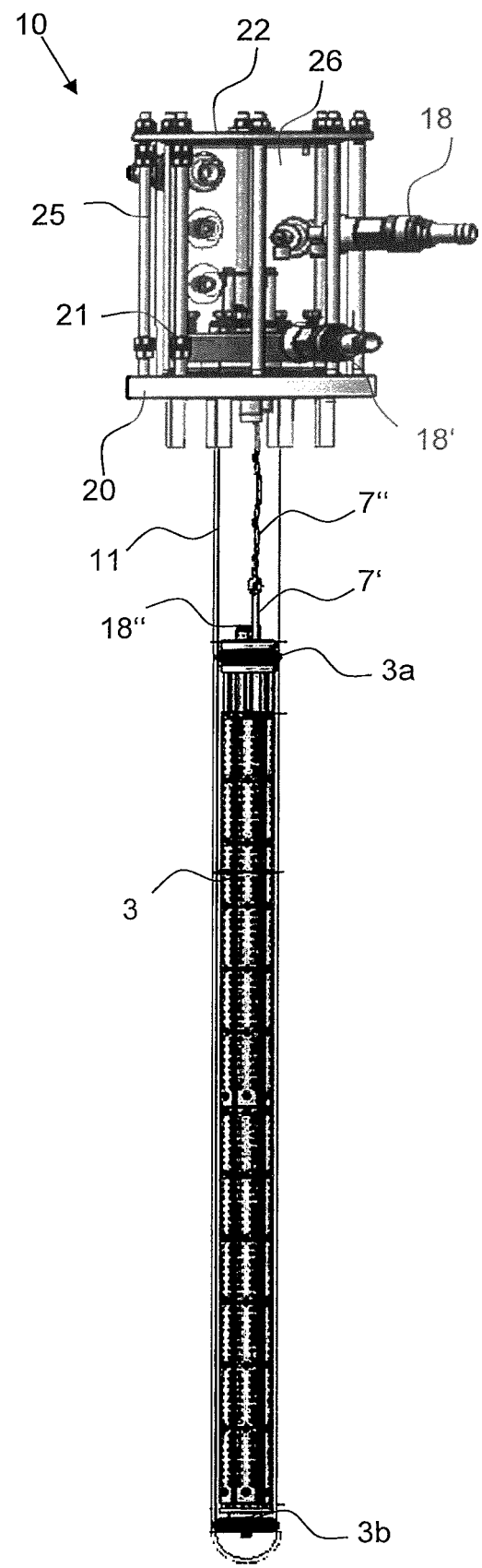
FIG. 15 a side view of an LED lamp module according to the invention with the embodiments of FIGS. 9 to 13.

As illustrated in FIG. 10, for electrical/electronic contacting of a support body 3 furnished with LEDs 1 with a separate head part 12, the support body 3 (or a socket section 3a not illustrated in FIG. 10) as well as the head part 12 can comprise connection devices 7' facing each other that, as is illustrated in FIG. 15, are connected to an additional connection element 7", here in the form of a chain, which enables a relative movability between support part 3 and head part 12 and in this way avoids tensions that may occur, for example, as a result of thermal expansion effects.

Figure 11:
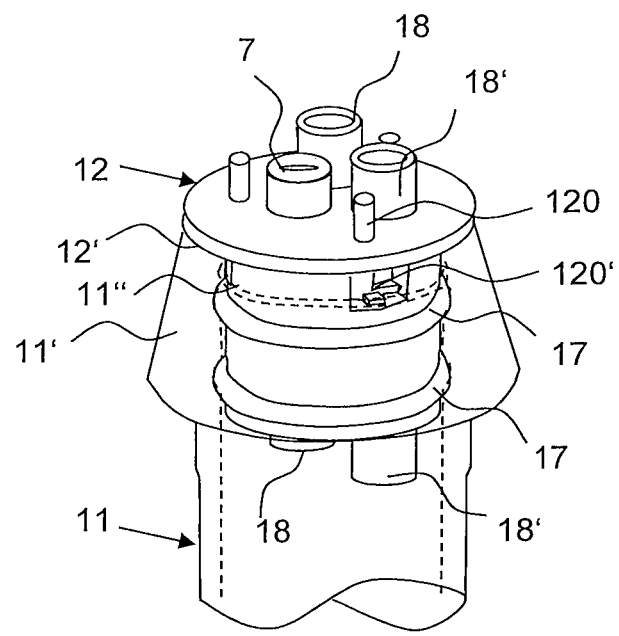
FIG. 11 a perspective detail view of the head part of FIG. 1 in the sealed arrangement at the open end of an immersion pipe according to a further embodiment of an LED module according to the invention.

In FIG. 10, moreover the connection lines 18, 18' at the head part 12 for supply and discharge of the non-conductive liquid, two axially spaced apart sealing rings 17 at the head part 12, and a flange section 12' are shown which closes off the head part 12 at the side facing away from the support body 3 and contributes to the seal-tight arrangement at the open end of the immersion pipe 11, as illustrated in the example of FIG. 11. The support body 3 comprises here a plurality of supply sections 4 which extend from the connection line section 18" which here is also to be connected by a line section, not illustrated, to the supplying connection line 18. The arrangement of the supply sections 4 corresponds with the arrangement of the LEDs 1 at the support body 3 in order to achieve an optimal and uniform backside cooling of the LEDs 1.

The open end of the immersion pipe 11 in FIG. 11 is formed with a cone-shaped collar 11' that widens away from the open end and in which the head part 12 is received. When the head part 12, as in the illustrated example, comprises a flange section 12', the latter can rest either, as in FIG. 11, on the end face of the open end of the immersion pipe 11 or on an annular shoulder, not illustrated, which is formed at the immersion pipe inner wall. For fixation of the head part 12 and securing of the sealing action through the sealing rings 17 which are pressed against the immersion pipe inner wall, the head part 12 comprises pivot latches 120 whose wing section 120' by rotation of the pivot latch 120 engages an annular groove 11' which is configured at the immersion pipe inner wall.

Figure 14:
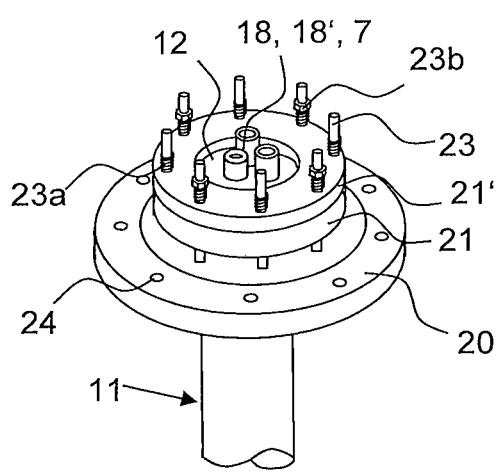
FIG. 14 a perspective detail view of a fastening of the head part at the immersion pipe as an alternative to FIG. 11.

As an alternative to the fastening with the pivot latches 120 which provide for a point fastening action, preferably a pressure ring 21' can be provided, as illustrated in the example of FIG. 14, that has an opening with a diameter that is smaller than the diameter of the head part 12 so that the pressure ring 21' can contact circumferentially and areally a ring section on the head part 12 and hold it in the open end of the immersion pipe 11 when the pressure ring 21' is fastened with the holding ring 21 for the immersion pipe 11 at a base plate 20, which will be described in the following. Access to the connection lines 18, 18' and the electrical connection device 7 remains available through the opening of the pressure ring 21'.

Figure 12:
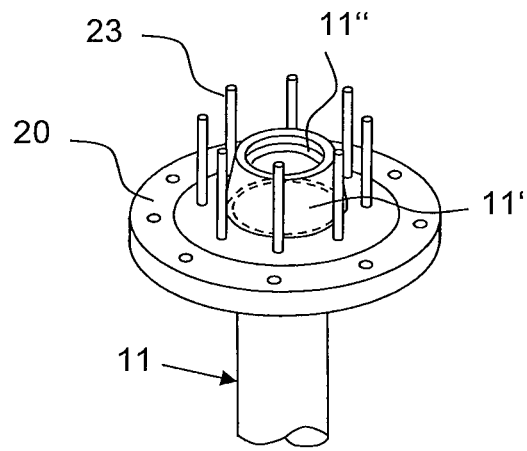
FIG. 12 a perspective detail view of an immersion pipe arranged in a base ring.
Figure 13:
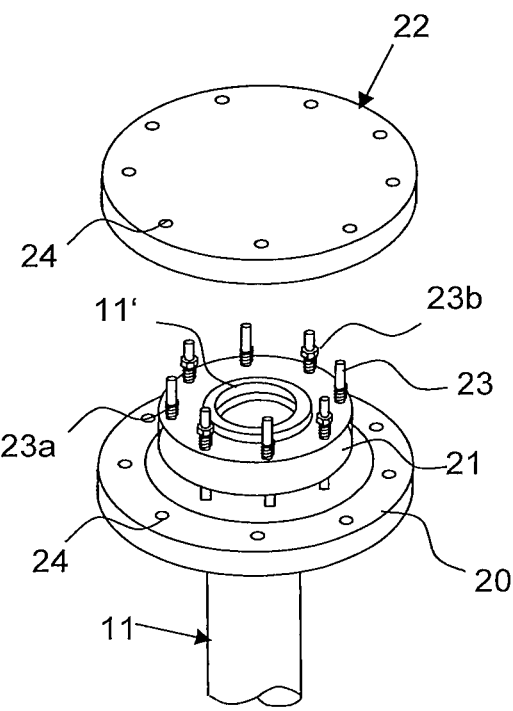
FIG. 13 a perspective detail view of a mounting step that follows FIG. 12 in which the immersion pipe is fastened by a pressure ring at the base ring.

In order to provide an LED lamp 10, as shown in FIG. 15, in a ready-to-use state, for example, for use in a reactor (not illustrated), the immersion pipe 11 (compare FIG. 12) that comprises a cone-shaped collar 11' can be arranged in an opening of a base plate 20 wherein the diameter of the opening is matched to the outer diameter of the immersion pipe 11 so that the collar 11' of the immersion pipe 11 is resting on the base plate 20. In FIGS. 12 to 14, the base plate 20 is designed as a base ring 20 but, of course, deviating shapes are conceivable here also as long as the opening in the base plate 20 is suitable for receiving the immersion pipe 11. For fixation of the immersion pipe 11 at the base plate 20, a holding ring 21 is placed onto the cone-shaped collar 11' (FIG. 13) wherein the holding ring 21 comprises a cone-shaped opening that is configured to correspond to the collar 11' and is held at the base ring 20 by means of bolts 23 and nuts 23b. In order to compensate here also different expansions that may occur due to a temperature effect, the holding ring 21 is not rigidly fixed but springs 23a are arranged on the bolts 23 between the holding ring 21 and the nuts 23b which force the holding ring 21 against the collar 11 but, upon occurrence of a corresponding counter force, also enable a further compression and thus avoid tensions that are too great.

In the open end of the immersion pipe 11 in FIG. 13, the head part 12, after introduction of the support body 3 with the LEDs 1 in the immersion pipe 11, is arranged so as to seal and is fixed (compare FIG. 11) after the head part 12, if required, has been connected to the support body 3 electrically (connection devices 7', 7") and fluidly (connection line 18 and section 18"). Before finally the cover plate 22, if needed, with arrangement of a cylindrical housing 26, is connected to the base plate 20 by means of bolts 25 that are passed through the bores 24, the connection lines 18, 18' can be connected to the corresponding supply and discharge for the non-conductive liquid and the electrical connection device 7 to a corresponding electrical/electronic line (not illustrated).

The invention is not limited to the illustrated examples that show primarily a lamp module with an immersion pipe that is closed at one end in vertical arrangement. Of course, also deviating arrangements and immersion pipes with open ends at both ends are conceivable, wherein one end is connected to the head part and the other can be closed by a closure part.

Moreover, the embodiments and feature combinations that are illustrated in an exemplary fashion in the Figures are not intended to be limiting. Deviation in number and arrangement of the LEDs, shape, and dimensions of support body, head part, and immersion pipe as well as the deviating feature combinations with respect to the embodiment with heat conducting structures, cooling agent circuits, and electrical connection devices etc. are encompassed by the claimed subject matter.

In general, an LED lamp module according to the invention, as illustrated in FIG. 6, can comprise one or a plurality of temperature sensors on the support structure or the circuit board which ensures a protective shutdown for protection of the semiconductor components when the maximally permissible ambient temperature is surpassed. When dropping below the maximum temperature, the control device can automatically switch on again the corresponding LEDs. Also, in case of failure of an LED of a circuit board, sensors can detect this and effect in the control device a switch-off action of the circuit board or separation from the current circuit with simultaneous adjustment of the total current strength. Such an LED failure is accompanied by a temperature hotspot which upon a chain reaction and failure of a plurality of LEDs can lead shortly to an excessive limit temperature which is therefore to be avoided. The further circuit boards can be continued to be operated with limited current strength so that a total loss of the lamp module is prevented. All safety-relevant sensors of the lamp module can be configured with redundancy or with two channels in order to realize the corresponding required SIL class.

In FIG. 6, moreover a detection unit E is illustrated which is provided for determining a failure of an LED 1. The detection unit E is arranged on the circuit board 30 and is configured to determine a failure of one or a plurality of LEDs 1 on the support circuit board 30 and communicate it to the current supply and control unit 16 that, depending on a detected failure, interrupts the current supply for the circuit board 30 in question and limits it for the further support circuit boards 30.

Since the LEDs are accommodated in groups on the support structures, they can be individually exchanged upon failure.

Moreover, the lamp module according to the invention is suitable to provide process-specific spectra wherein moreover by means of the control circuit the radiation intensity can be adjusted to the photochemical process. Thus, a power control of the LEDs (dimming) can be realized for process control because in many reactions the absorption will change during the process. This can be responded to by targeted measuring and control circuits and lamp dimming in order to realize an efficient system and to avoid excessive irradiation.

A lamp module according to the invention can comprise monochromatic LEDs as well as a mixture of LEDs with different emission spectra that provide for the optimal utilization of the absorption spectrum of the respective reaction. The same applies when the immersion lamps are to be used for bioreactors. Here, LEDs with different emission wavelengths can be implemented on a support structure in order to achieve optimal growth rates. In different growth phases or different cells, optimally mixed light spectra and intensities can be respectively provided for optimized growth.

The non-conductive liquid that is used in the lamp module according to the invention is selected then depending on the emission spectrum of the LED so that the non-conductive liquid exhibits a sufficient transmission in order to provide the improved total light output of the lamp module.

LIST OF REFERENCE CHARACTERS

1 LED, OLED
1' LED without primary optic
1*a* primary optic/plastic lens
1*b* semiconductor crystal
1*c* wire
1*d* anode
1*e* LED chip/phosphorus layer
1*f* cathode
1*g* support
2 heat conducting structure
3 support body
3', 3" inner structure, opening
3*a*, 3*b* socket section
3*c* annular spring
4 cooling supply section
5 lengthwise water-tight connector
6 chamber
7, 7' electrical connection device
7" connection element
9 mechanical connection device
10 lamp module
11 immersion pipe
11', 11" conical collar, annular groove
12 head part
12' flange section
120 pivot latch
120' wing section
14 holder
15 current supply and/or control line
15' contact element
16 current supply and control device
17 seal
18, 18' circuit connection line
18" connection section
19 immersion pipe interior
20 base rating
21 holding ring
21' pressure ring
22 cover plate
23 stud bolt
23*a* spring
23*b* nut
24 bore
25 bolt
26 housing
30 support circuit board
100 non-conductive liquid
A fitting
AT breathing unit with drying agent
E detection unit
F flow meter
P pump
S control unit
T temperature sensor
WT heat exchanger

What is claimed is:

1. Lamp module (10) that is configured to be used as an immersion radiator in photochemical reactors, that comprises a support body (3) with at least one light-emitting diode (LED) (1) and a head part (12) for electrical connection of the at least one LED (1) and for holding the support body (3) and an immersion pipe (11) that delimits an immersion pipe interior (19) in which the support body (3) with the at least one LED (1) is arranged, wherein the head part (12) comprises connection lines (18, 18') for the supply and the discharge of a cooling liquid, and the support body (3) is configured as a cooling body that delimits at least one internal fluid path as supply section (4) for the cooling liquid, wherein the supply section (4) is connected through the head part (12) to a first connection line (18), characterized in that the cooling liquid is an electrically non-conductive liquid (100) that is transparent for the wavelengths of the radiation emitted by the LEDs (1) of the lamp module (10), and the immersion pipe interior (19) delimited by the immersion pipe (11) is filled with the electrically non-conductive liquid (100) such that the at least one LED (1) is immersed completely in the non-conductive liquid (100), wherein the connection lines (18, 18') for the supply and the discharge of the non-conductive liquid (100) communicate with the immersion pipe interior (19), wherein the supply section (4) that is connected through the head part (12) to the first connection line (18, 18') opens at a side of the support body (3) facing away from the head part (12) into the immersion pipe interior (19), and wherein a second connection line (18') that extends through the head part (12) opens at the head part (12) toward the immersion pipe interior (19), wherein the connection lines (18, 18') are connected for forming a circuit of the non-conductive liquid (100), wherein the circuit comprises at least one heat exchanger (WT) and a conveying device (P).

2. Lamp module (10) according to claim 1, characterized in that the head part (12) is connected by means of at least one seal (17) sealingly to an open end of the immersion pipe (11), wherein the sealing connection is preferably spring-supported and/or a form fit connection.

3. Lamp module (10) according to claim 2, characterized in that the lamp module (10) comprises additionally a flow meter (F), wherein the flow meter (F) is connected to a control unit (S) that is configured to control the conveying device (P) and/or a fitting (A) provided at one of the connection lines (18, 18') depending on the flow values measured by the flow meter (F) in order to maintain a predetermined flow rate of the non-conductive liquid (100) through the immersion pipe interior (19) along a surface of the LEDs (1).

4. Lamp module (10) according to claim 3, characterized in that the flow meter (F) is a mass flow meter.

5. Lamp module (10) according to claim 4, characterized in that the mass flow meter is a Coriolis mass flow meter or a floating body flow meter.

6. Lamp module (10) according to claim 1, characterized in that the immersion pipe (11) with the head part (12) at the open end comprises a cone-shaped collar (11') widening away from the open end, which is held by a holding ring (21) with a corresponding cone-shaped opening at a base ring (20) by means of spring-loaded bolts (23), wherein the head part (12) is received in the open end of the immersion pipe (11) and is fastened seal-tightly by pivot latches (120) that can be brought into engagement with an annular groove (11") at an inner wall of the immersion pipe (11), or preferably by a pressure ring (21') whose opening has a diameter that is smaller than the diameter of the head part (12) and which is arranged on the holding ring (21) and together with the holding ring (21) is held at a base ring (20) by means of spring-loaded bolts (23).

7. Lamp module (10) according to claim 1, characterized in that the non-conductive liquid (100) is selected from highly refined mineral oils, silicone oils, and synthetic ester or ether compounds, wherein the non-conductive liquid (100) comprises a viscosity at 25° C. of 5 to 60 cSt.

8. Lamp module (10) according to claim 7, characterized in that the viscosity at 25° C. is 20 to 50 cSt.

9. Lamp module (10) according to claim 1, characterized in that the head part (12) and/or the support body (3) comprises heat dissipating structures (2).

10. Lamp module (10) according to claim 1, characterized in that the immersion pipe (11) is a double-wall immersion pipe (11) or the lamp module (10) comprises a second immersion pipe in which the first immersion pipe (11) is arranged.

11. Lamp module (10) according to claim 1, characterized in that the support body (3) comprises at least one chamber (6) through which at least one current supply and/or control line (15) extends from the head end of the support body (3) to a contact element (15') of the at least one LED (1).

12. Lamp module (10) according to claim 11, characterized in that the head part (12) comprises at least one electrical connection device (7) wherein preferably the head part (12) contains a current supply and control device (16) for the at least one LED (1) of the lamp module (10) and the at least one current supply and/or control line (15) is connected via the current supply and control device (16) to the at least one electrical connection device (7), and wherein preferably the connection lines (18, 18') extending through the head part (12) are configured for cooling the current supply and control device (16), and/or at least one mechanical connection device (9), for connecting the head part (12) to a holder (14), is present at the head part (12).

13. Lamp module (10) according to claim 1, characterized in that the lamp module (10) comprises a multitude of LEDs (1) wherein, respectively, a portion of the multitude of the LEDs (1) are arranged on a support circuit board (30), respectively, and the support circuit boards (30) are fastened to the support body (3).

14. Lamp module (10) according to claim 13, characterized in that the lamp module (10) comprises at least one temperature sensor that is arranged on the support body (3) or the support circuit board (30) and is connected to a current supply and control device (16) of the lamp module (10) that comprises a protective switch for the LEDs (1), and/or in that the lamp module (10) comprises a detection unit (E) for determining a failure of at least one LED (1) that is connected to the current supply and control device (16) of the lamp module (10) and is configured to determine a failure of one or a plurality of the LEDs (1) on the support body (3) or one of the support circuit boards (30), wherein the detection unit (E) or the current supply and control device (16) is configured to delimit or to interrupt, depending on a determined failure, the current supply for the further LEDs (1) or the further support circuit boards (30), and/or in that the current supply and control device (16) comprises at least one control circuit for an LED control with which same type or different LEDs (1) can be dimmed and/or the spectrum of the emitted wavelengths of different LEDs (1) can be changed.

15. Lamp module (10) according to claim 1, characterized in that the lamp module (10) comprises a breathing unit with drying agent (AT) in one of the connection lines (18, 18').

16. Lamp module (10) according claim 1, characterized in that at least one LED (1) of the lamp module (10), preferably all LEDs (1) of the lamp module (10), are configured without primary optic (1 a).

17. Photoreactor with a lamp arranged therein with an emission spectrum suitable for the photochemical reaction, characterized in that the lamp is a lamp module (10) according to claim 1.

* * * * *